United States Patent
Francke et al.

(10) Patent No.: US 6,873,682 B2
(45) Date of Patent: Mar. 29, 2005

(54) EXPOSURE CONTROL IN SCANNING-BASED DETECTION OF IONIZING RADIATION

(75) Inventors: Tom Francke, Sollentuna (SE); Stefan Thunberg, Lidingö (SE)

(73) Assignee: XCounter AB, Danderyd (SE)

( * ) Notice: Subject to any disclaimer, the term of this patent is extended or adjusted under 35 U.S.C. 154(b) by 0 days.

(21) Appl. No.: 10/754,698

(22) Filed: Jan. 12, 2004

(65) Prior Publication Data

US 2004/0141588 A1 Jul. 22, 2004

Related U.S. Application Data

(63) Continuation of application No. 10/115,965, filed on Apr. 5, 2002, now abandoned.

(30) Foreign Application Priority Data

Mar. 12, 2002 (SE) .............................................. 0200731

(51) Int. Cl.[7] .............................................. H05G 1/38
(52) U.S. Cl. ............................ 378/97; 378/96; 378/108
(58) Field of Search ............................ 378/37, 96, 97, 378/108, 109, 110, 111, 112, 95

(56) References Cited

U.S. PATENT DOCUMENTS

| | | | |
|---|---|---|---|
| 4,086,486 A | 4/1978 | Bybee et al. | |
| 4,185,195 A | 1/1980 | Moore | |
| 4,380,817 A | 4/1983 | Harding et al. | |
| 4,426,721 A | 1/1984 | Wang | |
| 4,744,099 A | 5/1988 | Huettenrauch et al. | |
| 4,953,189 A | 8/1990 | Wang | |
| 5,008,914 A | 4/1991 | Moore | |
| RE33,634 E | 7/1991 | Yanaki | |
| 5,177,776 A | 1/1993 | Ohmori | |
| 5,335,257 A | 8/1994 | Stunberg | |
| 5,828,408 A | 10/1998 | Mottin et al. | |
| 5,959,302 A * | 9/1999 | Charpak | 250/385.1 |
| 6,031,892 A | 2/2000 | Karellas | |
| 6,118,125 A | 9/2000 | Carlson et al. | |
| 6,256,406 B1 | 7/2001 | Garland et al. | |
| 6,337,482 B1 | 1/2002 | Francke | |
| 6,373,065 B1 | 4/2002 | Francke et al. | |
| 6,385,282 B1 | 5/2002 | Francke et al. | |
| 6,414,317 B1 | 7/2002 | Francke et al. | |
| 6,459,765 B1 * | 10/2002 | Ganin et al. | 378/108 |
| 2002/0003860 A1 | 1/2002 | Francke et al. | |

FOREIGN PATENT DOCUMENTS

WO   WO 00/62094   10/2000

* cited by examiner

Primary Examiner—David V. Bruce
Assistant Examiner—Hoon Song
(74) Attorney, Agent, or Firm—Harness, Dickey & Pierce, PLC

(57) ABSTRACT

An apparatus for recording a 2D image of an object comprises a plurality of 1D detector units, each exposed to ionizing radiation, as transmitted through or scattered off the object, and being arranged for 1D imaging of the radiation, to which it is exposed. The detector units are distributed in an array such that the 1D images of the radiation from the detector units are distributed over a substantial portion of the 2D image. The apparatus includes a device for moving the detector units relative the object while the detector units repeatedly detect to create the 2D image of the object; and a control device for controlling the detector units to detect ionizing radiation during a short period of time before or during an initial part of the movement; calculating an optimum exposure time for the repeated detection based on the short period of time detection; and controlling the repeated detection to automatically obtain the optimum exposure time.

58 Claims, 6 Drawing Sheets

EXPOSURE CONTROL IN SCANNING-BASED DETECTION OF IONIZING RADIATION

This application is a Continuation of U.S. Ser. No. 10/115,965 filed Apr. 5, 2002, which is now abandoned.

FIELD OF THE INVENTION

The invention relates generally to apparatuses and methods for scanning-based two-dimensional radiation detection, and more specifically the invention relates to automatic exposure control therein for achieving optimum image quality.

BACKGROUND OF THE INVENTION AND RELATED ART

In digital medical X-ray diagnosis, the X-ray radiation time, energy and flux employed must be carefully controlled to achieve optimum quality of the images recorded.

The exposure has to be selected such that the images possess high signal-to-noise ratio, and high dynamic range without being overexposed, i.e. that the detector saturates.

One method of controlling the exposure of a sensitive two-dimensional detector array, such as a CCD, is obviously to record an image, analyze it with respect to signal strengths and contrast achieved, and then adjust the exposure, whereafter a second high-quality image is recorded. While such an approach provides for the recording of high-quality images, it nevertheless suffers from a few drawbacks. Firstly, the method is time consuming: two read-outs have to be made for each object area to be imaged with intermediate analysis and adjustments. Further, the radiation dose to the object area to be imaged is higher, since it is exposed to radiation twice.

Another method, disclosed in U.S. Re. 33,634 by Yanaki, samples the radiation passed through an object to be examined during a short portion of the total exposure time by means of a sensor and adjust exposure time and the voltage, current and focal spot size of the X-ray source so that the radiation delivered by the X-ray tube during the remainder of the exposure will produce optimum contrast between structures within the object examined and optimum darkening of a film, xerographic picture, fluoroscopic image, or other recording medium. The method accounts for variations in absorption coefficient between one object to be radiographed and the next.

SUMMARY OF THE INVENTION

One drawback of the technique disclosed by Yanaki is that a sensor is needed in addition to the recording medium for the production of a two-dimensional image. Such solution is unnecessary complicated and the sensor and the recording medium may have different sensitivities, different dynamic ranges, and different noise levels, which can make the calibration and the exposure control more complicated.

A further drawback is that the sensor employed lacks capabilities of sensing signal strengths at different positions of the image simultaneously and/or capabilities of sensing a differential signal with high spatial resolution, which are needed in order to obtain the signal strength of the object region having the highest density and thus highest absorption and the variations in signal strengths across the image, and not only a spatially integrated single value of the signal strength.

A main object of the invention is therefore to provide an ionizing radiation detecting apparatus and method including an automatic exposure control, which overcome the limitations associated with the prior art.

In this respect there is a particular object to provide such an apparatus and such a method, which are uncomplicated and can still produce high-quality images with excellent signal-to-noise ratios, dynamic range, and image contrast.

A further object of the invention is to provide such an apparatus and such a method, which optionally incorporate a shielding functionality integrated with said automatic exposure control for automatically shielding radiation passing outside the outer shape of an object to be recorded.

A yet further object of the invention is to provide such an apparatus and such a method, which are reliable, accurate, precise and inexpensive.

A still further object of the invention is to provide such an apparatus, which is suitable for volume production and which has a long lifetime.

These objects, among others, are attained by apparatuses and methods as claimed in the appended claims.

The inventors have found that by arranging smaller one-dimensional radiation detector units in an array, a scanning-based detector apparatus for highly resolved two-dimensional imaging of objects, such as e.g. breasts in mammography examinations, is provided, which is extremely well suited for fast and sophisticated automatic exposure control. The detector units are distributed in the array such that the one-dimensional images of the radiation from the plurality of one-dimensional detector units are distributed over a substantial portion of the two-dimensional image of the object, which is to be recorded. The detector units may be arranged in a dense two-dimensional array of rows and stacks, which reduces scanning distance and provides macroscopic structure information of the whole object area to be imaged without scanning. The detector units may alternatively be arranged in other patterns, e.g. in a circle, where each detector unit is oriented essentially radially with respect to the circle.

By means of detecting ionizing radiation by the array of one-dimensional detector units during a short period of time before or during an initial part of a scan a picture of line images distributed over a substantial portion of the picture is obtained very fast, which is excellent for deriving information of the object to be scanned, such as e.g. average, maximum and minimum density of the object.

An optimum exposure time for each readout during the subsequent scan or the remainder of the scan is then calculated based on information deduced from the picture of line images and on the short period of time, wherafter this optimum exposure time is employed for each readout during the scan or the remainder thereof. Hereby, an optimum image quality is achieved.

The exposure time can be calculated from a minimum or average signal value in the picture of line images or in a limited area thereof or from a sophisticated algorithm based on e.g. the histogram of the picture of line images. Preferably, a minimum or average signal value is deduced from a number of nearby line images having the lowest average signal strength (corresponding to the most absorbing part of the object to be scanned).

Preferably, a look-up table of desired signal strengths for various object characteristics (e.g. different compressed breast thicknesses) is provided, and a characteristic of the object, of which a two-dimensional image is to be recorded, is received from e.g. a sensor or an operator of the apparatus, wherafter the optimum exposure time is calculated by means of multiplying the short period of time with the ratio of the desired signal strength and a signal strength as obtained from the picture of line images.

Another inventive feature that may optionally be incorporated is a collimator device with a variable aperture arranged in the path of the ionizing radiation upstream of the object. By means of the picture of line images, an outer shape of the object can be determined, and the variable aperture is adjusted to shield radiation not interacting with the object.

Further characteristics of the invention, and advantages thereof, will be evident from the detailed description of preferred embodiments of the present invention given hereinafter and the accompanying FIGS. 1–6, which are given by way of illustration only, and thus are not limitative of the present invention.

It shall be particularly emphasized that while the present invention is described in detail as regarding X-ray radiation and X-ray tubes the present invention is mutatis mutandis applicable for other kinds of ionizing radiation and ionizing radiation sources.

Further, the invention is primarily focused on medical applications and mammography in particular, but it is nevertheless useful for other kind of industrial applications including such as non-destructive testing and inspection e.g. of printed circuit boards and pipelines. Thus, while the object to be imaged will be referred to as a breast in the description below, it shall be appreciated that it can be exchanged for virtually any kind of materia without departuring from the present invention.

DESCRIPTION OF PREFERRED EMBODIMENTS

Figure 1:
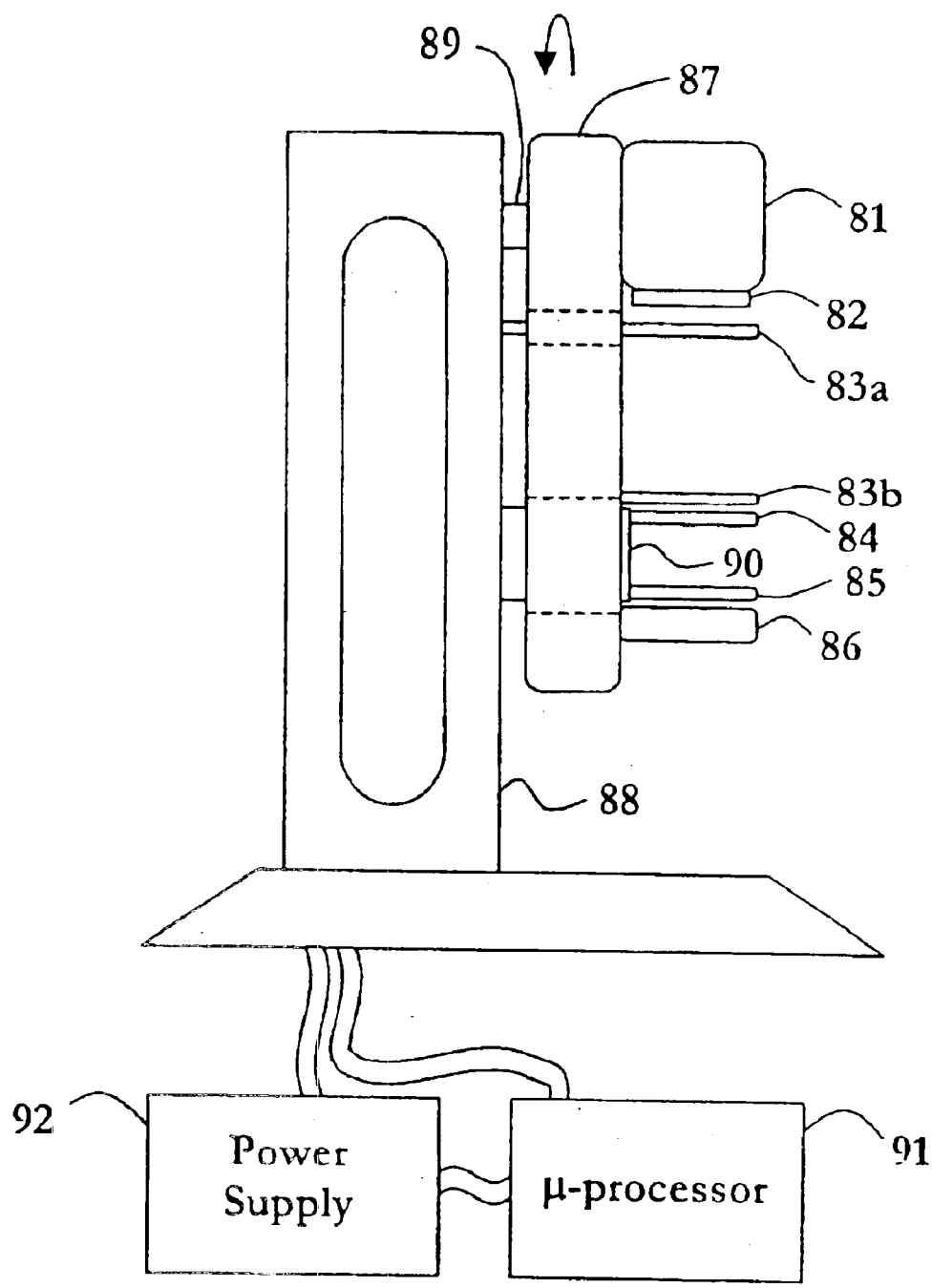
FIG. 1 illustrates schematically, in a side view, a device for X-ray examinations according to a preferred embodiment of the present invention.

With reference to FIG. 1, which illustrates schematically, in a side view, a device preferably designed for mammography examinations a preferred embodiment of the present invention will be described.

From top to bottom the device comprises an X-ray source 81, a filter device 82, a collimator device 83a, a fan beam collimator 83b, a compression plate 84 and an object table 85, and a scanning-based detector arrangement 86 including a plurality of one-dimensional detector units.

The X-ray source 81 is a conventional X-ray tube having a cathode, which emits electrons, and an anode, on which said electrons impinge, and which is a source of X-rays, said tube having an operating voltage, which is the voltage drop between said anode and said cathode, a tube current, which is the current between said anode and said cathode, and a focal spot size, which is the area of said anode on which said electrons impinge.

The operation voltage, tube current and/or focal spot size may be adjustable. By applying a lower peak voltage to the X-ray tube lower energy X-ray photons are produced, which are more easily absorbed by any tissue. By increasing the current from cathode to anode in the X-ray tube the X-ray flux is increased proportionally. By increasing the size of the focal spot, the power rating of the X-ray tube can be increased. For further details regarding the effect of operation voltage, tube current and focal spot size on radiography examinations reference is made to the Yanaki patent (U.S. Re. 33,634), the content of which being hereby incorporated by reference.

Just beneath the X-ray tube are placed a filter device 82 typically including thin metallic foils acting as filters to absorb the lowest (and sometimes also the highest) energy photons, which do not contribute significantly to the image quality but do increase the radiation dose to the patient. The filter device may have variable spectral transmission characteristics.

The collimator device 83a is radiation absorbing, but has a radiation transparent controllable variable aperture, whereby large amounts of radiation, which are not needed for the examination, may be stopped before reaching the level of the examination object, i.e. the breast in mammography examinations. Hereby, the amount of scattered radiation, which increases the dose to the patient and reduces the contrast in the image, is reduced.

Figure 2:
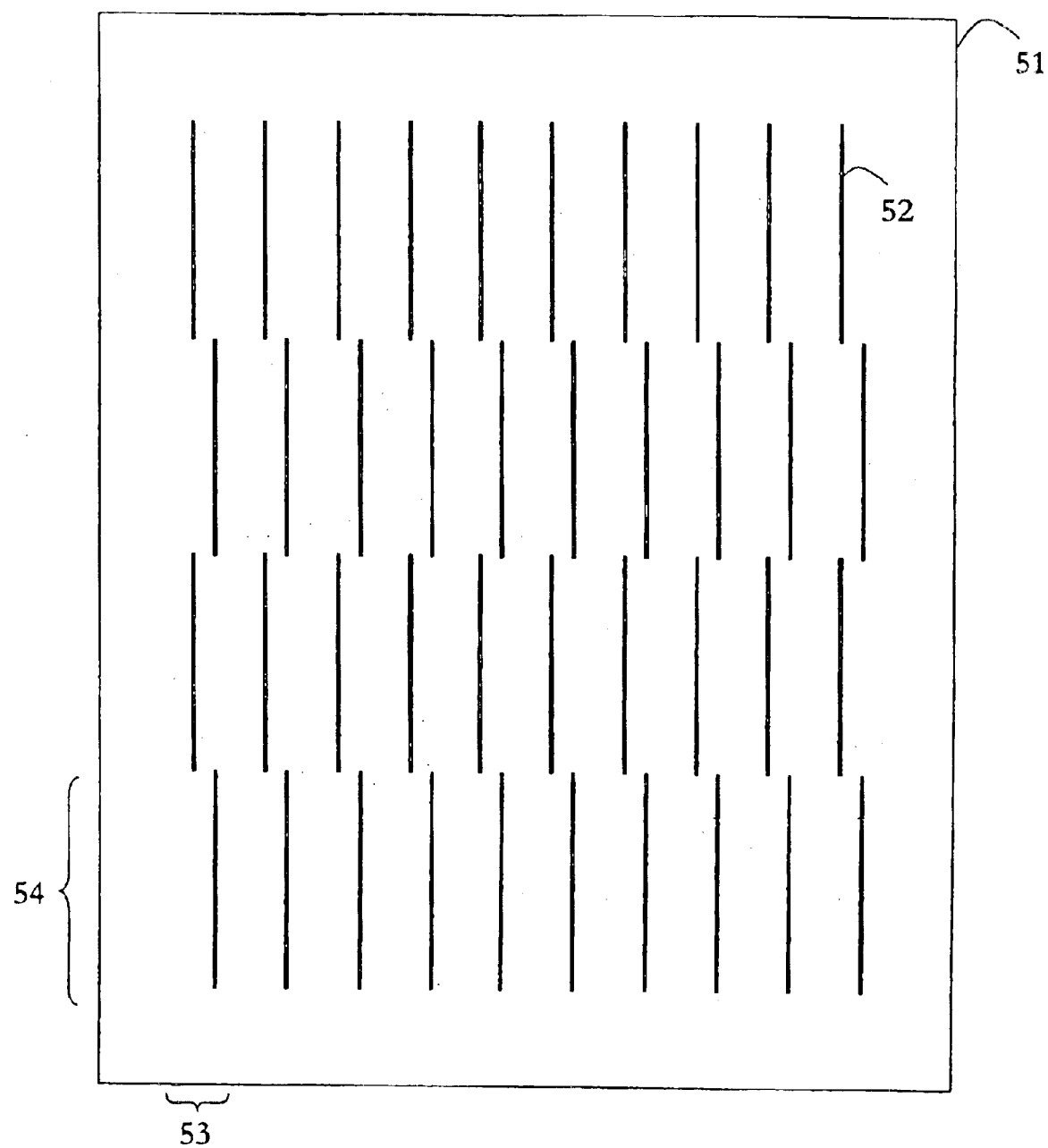
FIG. 2 is a schematic plan view of a fan beam collimator as being comprised in the device of FIG. 1.

The fan beam collimator 83b, schematically illustrated in FIG. 2, may be a thin foil 51 of e.g. tungsten with multiple narrow radiation transparent slits 52 etched away. The slits are arranged in rows 53 and stacks 54 and are aligned with corresponding line-shaped sensitive areas or entrance slits of the detector units of the detector arrangement such that X-rays passing through each slit 52 will reach a corresponding sensitive area or the detector arrangement. The purpose of this collimator is to reduce the radiation dose to the breast being examined.

Figure 3:
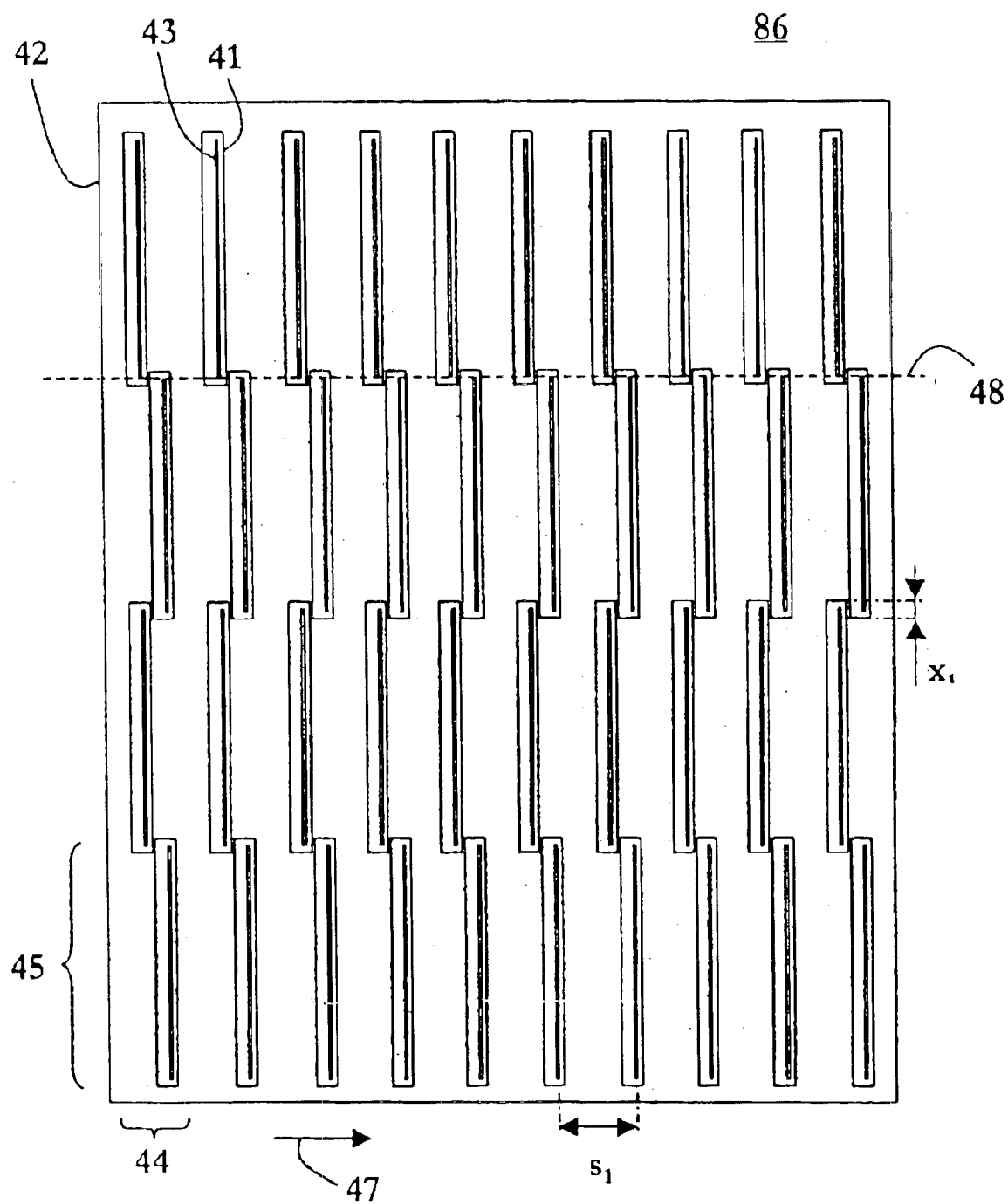
FIG. 3 illustrates schematically, in a front view, a scanning-based detector arrangement as being comprised in the device of FIG. 1.

The detector arrangement 86 is illustrated in FIG. 3 and includes a plurality of one-dimensional detector units 41 arranged on a common support structure 42 in a two-dimensional array of rows 44 and stacks 45 with their respective sensitive areas or entrance slits 43 facing the front of the arrangement. For illustrative purposes a matrix of only 4×10 detector units is illustrated, i.e. each row 44 includes four detector units and each stack 45 includes ten detector units, even though it shall be appreciated that the arrangement may include many more units. For instance if the detector units are spaced apart by $S_1$=5 mm (from detector unit to detector unit) and an area of typically 20×20 to 50×50 $cm^2$ shall be covered each stack may include 40–100 detector units. The width of each line detector unit may for instance be 40–60 mm, and thus typically 5–12 detector units are arranged in each row.

Further the detector arrangement of FIG. 3 may include side and front covers (not explicitly illustrated).

During the mammography examination the breast is compressed between the compression plate 84 and the object table 85, where the compression plate 84 for that purpose is movable in the vertical direction and lockable. If the device of FIG. 1 shall be used for other kind of measurements than mammography examinations the two compression plate. 84 and object table 85 may be exchanged by a holder or support for holding the particular object to be examined (not illustrated).

The X-ray tube 81, the fan beam collimator 83b and the detector arrangement 86 are attached to a common E-arm 87, which in turn is rotatably attached to a vertical stand 88 by means of a spindle 89 approximately at the height of the X-ray tube 81. In this manner, the X-ray tube 81, the fan beam collimator 83b and the detector arrangement 86 can be moved in a common pivoting movement relative to the breast to scan the breast and produce a two-dimensional image thereof. Assuming a distance of 5 mm between the detector units in each stack 45 of the detector arrangement (which correspond to the shortest possible scanning distance for recording a complete two-dimensional image) and a distance of 65 cm between the spindle 89 and the detector arrangement a scan corresponds typically to a rotation of about 0.44°, which typically may be performed in a few seconds. The scanning direction is indicated by arrow 47 in FIG. 3.

The collimator device 83a is firmly attached to the vertical stand 88, and the compression plate 84 and object table 85 are firmly attached to a support 90, which in turn is firmly attached to the vertical stand 88. For this purpose the E-arm 87 is provided with two recesses or similar in the E-arm 87 (illustrated by the dashed lines). During scanning, the collimator device 83a and the breast are kept still.

It shall be appreciated that the device of FIG. 1 may be modified and arranged for linear movement of the X-ray tube 81, the fan beam collimator 83b and the detector arrangement 86 with respect to the breast being examined.

It shall further be appreciated that the device of FIG. 1 may be modified such that the patient and the collimator device are moved during scanning, while the X-ray tube 81, the fan beam collimator 83b and the detector arrangement 86 are kept at rest.

It shall be noted that the detector units 41 in each row 44 of the detector arrangement of FIG. 3 are staggered. Since the detector units may not be capable of detecting at its extreme end portions, the units are staggered to cover the complete distance of 20–50 cm, avoiding any "dead" zones. Where the sensitive area or entrance slit 43 of one detector unit 41 ends, the sensitive area or entrance slit of a further detector unit begins in each row 44. This feature can be seen distinctly along dashed line 48 in FIG. 3 and calls for an overlap $x_1$ between the detector units, where $x_1$ may typically be at least 0.05–10 mm or larger.

It shall be appreciated that the line detector units are not necessarily arranged parallel with each other on a plane substrate, but are arranged to point towards the radiation source used such that radiation from the radiation source can enter the respective detector unit.

For the same purpose the fan beam collimator 83b has slits that are less spaced apart than the detector units and narrower that the detector unit entrance slits. The alignment between the radiation source (point source, line source or 2D source), the fan beam collimator 83b and the detector arrangement 86 provides for multiple planar radiation beams from the radiation source passing through the fan beam collimator 83b 51 and into the individual detector units 41 of the detector arrangement 86.

For further details regarding arrays of detector units and the detector units themselves, reference is made to our pending Swedish patent application No. 0200447-1 entitled Radiation detector arrangement and filed on Feb. 15, 2001, the content of which being hereby incorporated by reference.

Further, the device comprises a microprocessor or computer 91 provided with suitable software for controlling the device and readout and post-processing of the signals from the line detector units and a power supply 92 for supplying the detector units and the microprocessor or computer 91 with power and for driving a step motor or similar housed in the vertical stand 88 for driving the spindle 89 and thus the E-arm 87.

In operation, X-rays are emitted from the X-ray tube 81 and pass through the filter device 82. The collimator 83a and the fan beam collimator 83b absorb most of the X-rays. Only x-rays passing through the slits of the fan beam collimator 83b traverse the breast. In the breast, the X-ray photons can be transmitted, absorbed or scattered. The X-rays that are transmitted leave the breast and enter into the detector units 41 of the detector arrangement 86 and are detected.

During scanning, the E-arm 87, holding the X-ray source 81, the fan beam collimator 83b and the detector arrangement 86, is moved in a pivoting movement such that the detector arrangement scans across the breast in a direction, which is essentially parallel with the compression plate 84 and object table 85 and parallel with the chest wall.

Each line detector unit is continuously detecting X-rays. At regular movement intervals, typically every 10–50 micrometer, the detected signals are read out and stored in a memory of the microprocessor 91. In this way, each line detector unit gives a number of line images of the breast. When the X-ray source and the scanning are stopped, all these image segments are grouped together by the microprocessor 91 to form a two-dimensional image.

In an alternative scanning technique the array of one-dimensional detector units is moved relative the breast stepwise, and the one-dimensional detector units are detecting while the array of one-dimensional detector units is kept still between the stepwise movements.

According to the present invention the device of FIG. 1 is provided with an automatic exposure control preferably implemented in microprocessor 91 by means of appropriate software. In the most general version the microprocessor 91 is adapted to perform the following actions:

(i) controlling the one-dimensional detector units to detect X-rays during a short period of time before or during an initial part of the scanning of the breast, where the short period of time typically is in the interval 100 ns–10 s, preferably in the interval 1 $\mu$s–100 ms, and most preferably 10 $\mu$s–10 ms;

(ii) calculating an optimum exposure time for each detection of the scan based on the detection of X-rays before or during an initial part of the scan; and (iii) controlling the scan so as to obtain the optimum exposure time for each of the detections during the scan to thereby obtain a two-dimensional image of the breast having optimum quality.

An important advantage of the exposure control implemented in the scanning-based detector arrangement is that as a result of the short period of time detection (pre-scan detection) a picture is obtained, which includes a plurality of one-dimensional images of the breast distributed over a substantial portion of the two-dimensional image of the breast, which is to be recorded during the subsequent scan. Thus, a very good knowledge of the breast and its macroscopic structure can be obtained very quickly with a minimum of dosage to the breast, which provides for an optimum setting of the exposure time for the remaining scanning.

Figure 5:
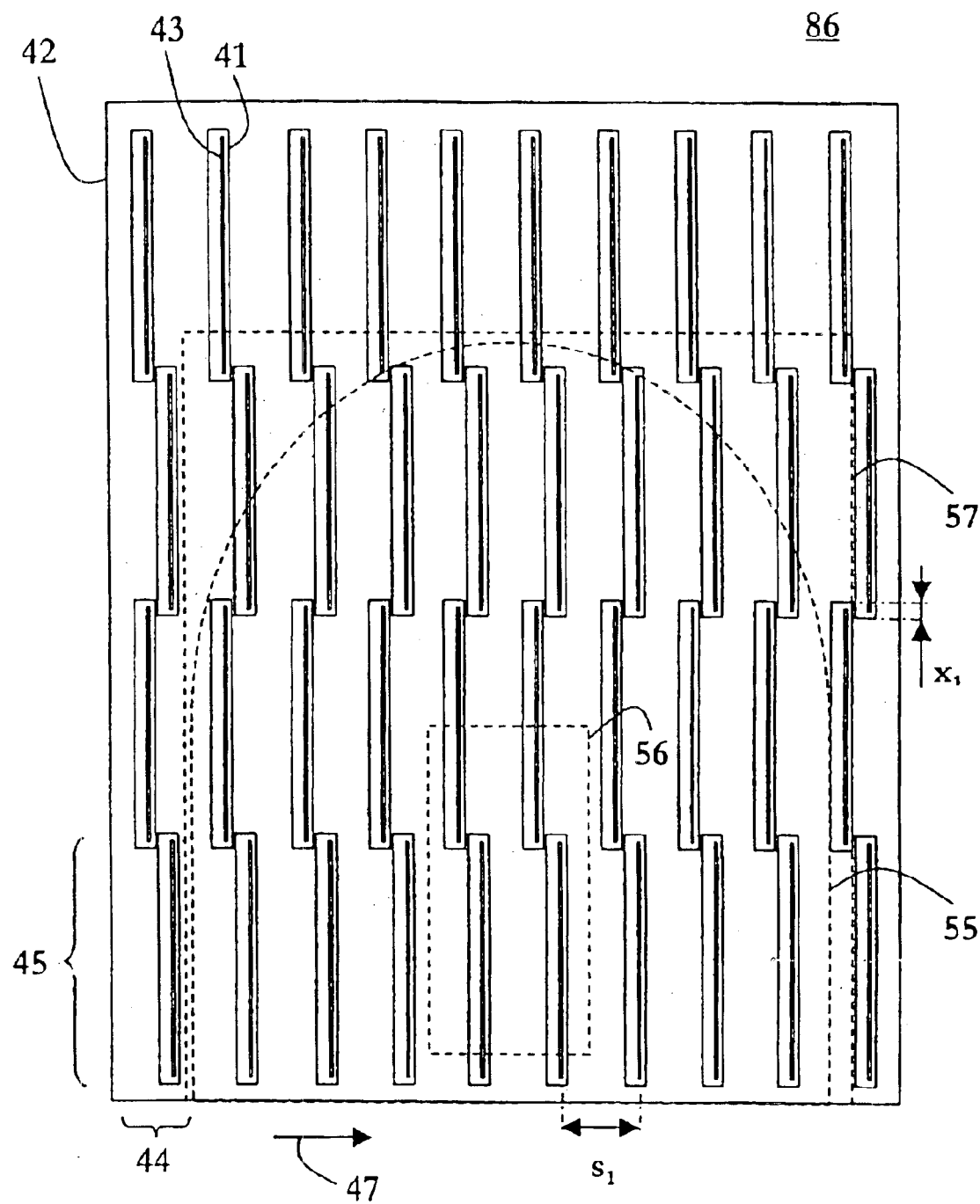
FIG. 5 illustrates schematically, in a front view, the scanning-based detector arrangement of FIG. 2, wherein shielding by a collimator device, as being comprised in the device of FIG. 1, is indicated.

The optimum exposure time for the scanning-based detection can be calculated based on a minimum or average signal value as obtained from the detection of X-rays before or during an initial part of the scan, or from a minimum or average signal value as obtained within a particular region of the picture of line images, e.g. within a centrally located region 56 as being illustrated in FIG. 5 or from a certain number of nearby line images. Such centrally located region 56 may have size of e.g. 2 cm×2 cm or 3 cm×3 cm. The region is preferably located where the signal strength is lowest (corresponding to the most absorbing portion of the imaged breast).

Alternatively, the optimum exposure time for the scanning-based detection can be calculated based on an integrated signal value of one or some of the one-dimensional detector units, e.g. of the unit with lowest integrated signal value.

Further, the speed, at which the array of one-dimensional detector units is moved relative the breast during scanning, may be adjusted depending on the detection of X-rays before or during an initial part of the scan or more particularly on the optimum exposure time calculated. If e.g. a very short optimum exposure time is calculated, this may indicate that the scanning shall be performed faster such that not an excessive amount of signal values are recorded.

Figure 4:
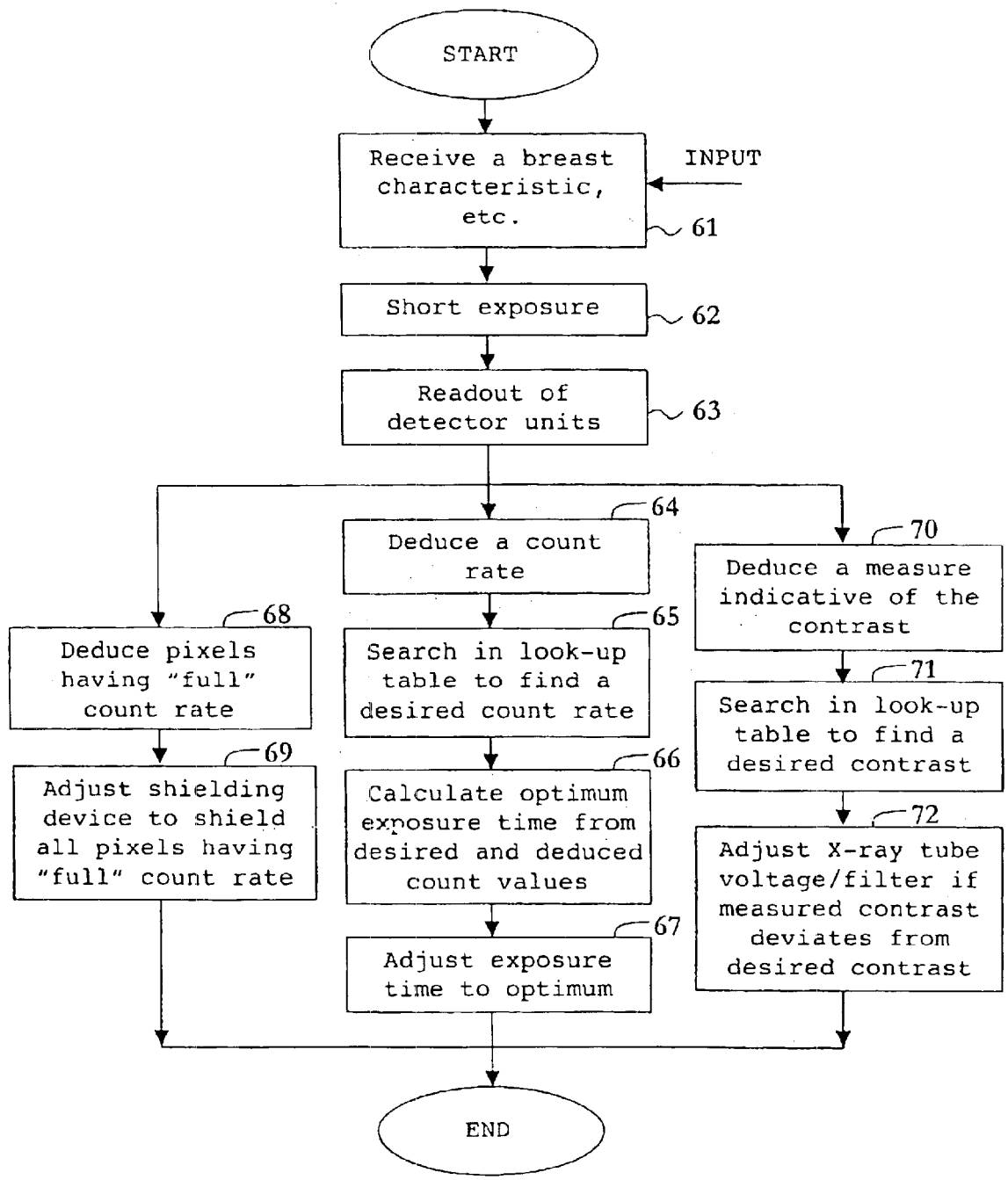
FIG. 4 is a flow chart of a method for automatic exposure control in the device of FIG. 1 according to a preferred embodiment of the present invention.

With reference now to FIG. 4, which is a flow chart of a method for automatic exposure control, a preferred embodiment of the present invention will be overviewed.

The method begins, in a step 61, with receiving a characteristic of the breast (or other object) to be imaged. This information may in the case of mammography be breast thickness in compressed state with a certain force applied to the compression plate. Alternatively, or complementary, to this the information may relate to the estimated density of the breast tissue, e.g. defined as its fat content versus glandular tissue. The information may be received by microprocessor 91 by means of being entered by an operator of the device or by means of being sensed by a sensor or similar (not illustrated). For instance, the distance between the compression plates would be easily measured by means of position sensors as well as the applied force.

Alternatively, the fat content versus glandular tissue of a breast may be determined from detections (by the arrangement 86 of multiple one-dimensional detectors) of two short exposures of the breast at two different compressed states (i.e. two different forces applied to the compression plate), since the fat content and glandular tissue have quite different absorption coefficients (not illustrated in the flow chart).

Thereafter, in a step 62, a short exposure of the breast under investigation is performed while the radiation transmitted is measured by the arrangement 86 of multiple one-dimensional detectors. The signals are, in a step 63, read out from the units and transferred to the microprocessor 91. Due to the construction of the detector arrangement, the detection and readout may be performed extremely fast.

From the signals, which represent a number of well distributed line images of the breast, a signal value, e.g. a count rate, is, in a step 64 deduced. This signal value may be deduced in a number of manners, e.g. as described above or by a sophisticated method taking the complete histogram and/or spatial signal information into account.

Next, a search is, in a step 65, performed in a look-up table stored in microprocessor 91, or in an accessible memory (not explicitly illustrated), which contains a table of desired signal strengths for various breast characteristics, and optionally thickness thereof, as being entered by the manufacturer of the device or by an operator. The desired signal strengths may be determined from calculations to achieve an optimum or acceptable signal-to-noise level, dynamic range or contrast of the subsequently recorded two-dimensional image, or they may be established by regulations.

The search is based on the input in step 61 and a desired signal strength for the scan is determined. Alternatively, instead of using a look-up table, the desired signal strength may be determined by means of employing an appropriate algorithm.

Then, in a step 66, an optimum exposure time for the breast at current settings is calculated based on the desired signal strength, the signal value deduced in step 64 and the exposure time used in step 62, and the exposure time setting is, in a step 67, adjusted to the optimum exposure time calculated, whereafter the method may be ended, and the device is ready to scan the breast.

A further feature of the method is that radiation not used for the scanning can be shielded. Thus, in a step 68 (which has to be performed after step 63, but may be performed independently of method steps 64–67) the picture elements (pixels) of the line images having a "full" signal strength, i.e. where no absorption at all has occurred, which in turn indicates that the X-rays are not transmitted through the breast, are deduced. Hereby, the outer shape of the breast may be determined. Then, in a step 69, the variable aperture of the collimator device 83*a* of the device of FIG. 1 is controlled to adjust to the outer shape of the breast, such that radiation not transmitted through the breast is stopped from passing through the collimator device. In such manner the amount of scattered radiation, which may increase the dose to the patient and reduce the image contrast, can med reduced.

A still further feature of the method is that the variable spectral transmission characteristics of the filter device 82 and/or the operation voltage of the X-ray tube 81 can be adjusted. Thus, in a step 70 (which has to be performed after step 63, but may be performed independently of method steps 64–67 and 68–69) a measure indicative of the contrast in the picture of the line images. Such measure is preferably related to the variations of the signal strengths of the picture elements (pixels) in the line images, or the signal strength of detected X-rays for different thicknesses of the breast as controlled by the compression unit.

Next, a search is, in a step 71, performed in a look-up table stored in microprocessor 91, or in an accessible memory (not explicitly illustrated), which contains a table of desired contrast levels e.g. for various breast characteristics. The search may be based on the input in step 61 and a desired contrast level for the scan is determined. Instead of using a look-up table, an appropriate algorithm may be applied to determine a desired contrast level.

The desired contrast level for the scan may in the case of mammography alternatively, or additionally, be based on (i) the change in compressed breast thickness caused by a change in compression force, and/or (ii) the signal levels as obtained from two exposures of the compressed breast at different compression forces.

Then, in a step 72, the measure indicative of the contrast in the picture of the line images is compared with the desired contrast level and based on this comparison the variable spectral transmission characteristics of the filter device 82 and/or the operation voltage of the X-ray tube 81 can be adjusted to obtain the desired contrast level in the subsequent scan.

Such adjustment may call for a further exposure time adjustment to take into account the altered spectrum of the X-rays transmitted through the breast and subsequently detected, and thus steps 62–67 may have to be repeated, e.g. using different filters and/or different compressions of the breast.

Yet further, if the optimum exposure time calculated in step 66 is very long an increase of the X-ray flux may be required. Very long exposure times may be unpleasant to a patient being examined, and further there is risk that the patient is moving and thus blurring the image recorded. Hence, the method as described above may be modified in the following manner.

If the optimum exposure time calculated in step 66 is longer than a particular threshold value (as set by the manufacturer or the operator possibly depending on the kind of measurement performed) then the tube current of the X-ray tube is increased and so is possibly also the focal spot size (not illustrated).

It shall be appreciated that the plurality of one-dimensional detector units 41 may be distributed arbitrary in an array as long as they are located such that the one-dimensional images of the ionizing radiation from them are distributed over a substantial portion of the two-dimensional image to be recorded.

Figure 6:
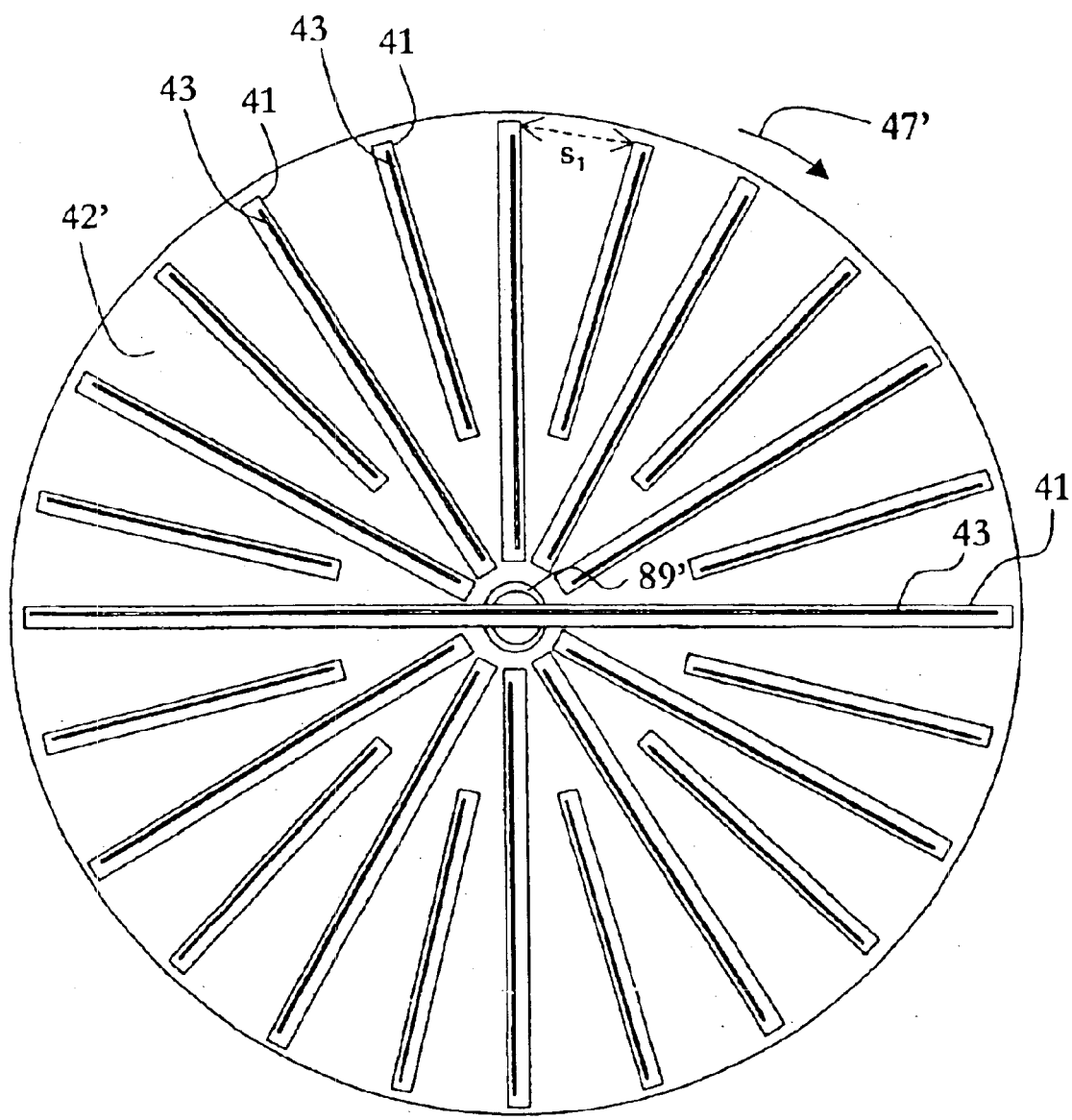
FIG. 6 illustrates schematically, in a front view, a scanning-based detector arrangement according to another preferred embodiment of the present invention.

For instance, detector units 41 may be arranged in a circle on a common circular support 42' as illustrated in FIG. 6, where each detector unit 41 is oriented essentially radially with respect to the circle and has its sensitive area or entrance slit 43 facing the front of the arrangement. The illustrated arrangement has one very wide detector unit arranged across the complete diameter of the support 42', ten less wider detector units symmetrically arranged with respect to the very wide unit, and twelve narrower detector units 41, each symmetrically arranged between two adjacent ones of the wider ones of the detector units.

This arrangement is during scanning rotated in the plane of the support 42' with respect to the breast or other object to be imaged as illustrated by arrow 47'. Preferably, the arrangement of FIG. 6 is rotated by means of a centrally located spindle 89' attached to the arrangement from the backside. One complete two-dimensional image may be recorded by rotating the array an angle corresponding to a circumferential distance $s_1$. If a fan beam collimator is to be used this has to be rotated together with the detector arrangement to keep the alignment during scanning.

For further details regarding such circular arrays of detector units, reference is made to our pending Swedish patent application No. 0200446-3 entitled Radiation detector arrangement and filed on Feb. 15, 2001, the content of which being hereby incorporated by reference.

It shall further be appreciated that the present invention is equally applicable for recording two-dimensional images of radiation as scattered off an object instead of being transmitted there through.

It shall still further be appreciated that the detector units of the of the present invention may of virtually any kind as long as they are one-dimensional detectors capable of recording one-dimensional images of the ionizing radiation, to which they are exposed.

However, a preferred line detector unit is the gaseous-based ionization detector, optionally provided with an electron avalanche amplifier, and particularly such gaseous-based ionization detector wherein the freed electrons are drifted in a direction essentially perpendicular to the direction of the incident ionization.

For further details regarding different kind of gaseous-based detector units for use in the present invention, reference is made to the following U.S. patent applications by Tom Francke et al. and assigned to XCounter AB, which applications are hereby incorporated by reference: Ser. Nos. 08/969,554 (issued as U.S. Pat. No. 6,118,125); Ser. Nos. 09/443,292; 09/443,320; 09/443,321; 09/444,569; 09/550,288; 09/551,603; 09/552,692; 09/698,174; 09/708,521; 09/716,228; and 09/760,748.

What is claimed is:

1. A scanning-based radiation detector apparatus for recording a two dimensional image of an object comprising a plurality of one-dimensional detector units, each exposed to ionizing radiation, as transmitted through or scattered off said object, and being arranged for one-dimensional imaging of the respective ionizing radiation, to which it is exposed, wherein said plurality of one-dimensional detector units are distributed in an array such that the one-dimensional images of the ionizing radiation from said plurality of one-dimensional detector units are distributed over a substantial portion of said two-dimensional image of an object to be recorded; and said scanning-based detector apparatus further includes:

a device for moving said array of one-dimensional detector units relative said object while the plurality of one-dimensional detector units are arranged to repeatedly detect to thereby create a two-dimensional image of the object; and a control device for controlling the movement of and the repeated detections by said array of one-dimensional detector units, said control device being adapted to control said array of one-dimensional detector units to detect ionizing radiation during a short period of time before or during an initial part of the movement, to calculate an optimum exposure time for each one of the repeated detections based on said detection of ionizing radiation before or during an initial part of the movement and said short period of time, and to control the repeated detections by said array of one-dimensional detector units to automatically obtain said optimum exposure time for each one of the repeated detections to thereby achieve optimum image quality.

2. The scanning-based radiation detector apparatus of claim 1 wherein said control device is adapted to calculate said optimum exposure time based on a minimum or average signal value as obtained from said detection of ionizing radiation before or during an initial part of the movement.

3. The scanning-based radiation detector apparatus of claim 1 wherein said control device is adapted to calculate said optimum exposure time based on a minimum or average signal value within a region of said array of one-dimensional detector units as obtained from said detection of ionizing radiation before or during an initial part of the movement.

4. The scanning-based radiation detector apparatus of claim 1 wherein said control device is adapted to calculate said optimum exposure time based on an integrated signal value of one or some of the one-dimensional detector units of said array of one-dimensional detector units.

5. The method of claim 4, wherein said control device is adapted to calculate said optimum exposure time based on the unit(s) with lowest integrated signal value, as obtained from said detection of ionizing radiation before or during an initial part of the movement.

6. The scanning-based radiation detector apparatus of claim 1 wherein said, control device is adapted to control said device for moving to move said array of one-dimensional detector units relative to said object continuously, while the plurality of one-dimensional detec- 7. The scanning-based radiation detector apparatus of claim 6 wherein said control device is adapted to control said device for moving to move said array of one-dimensional detector units relative to said object at a speed, which is based on said calculated optimum exposure time for each one of the repeated detections.

8. The scanning-based radiation detector apparatus of claim 1 wherein said control device is adapted to control said device for moving to move said array of one-dimensional detector units relative to said object stepwise; and to control the plurality of one-dimensional detector units to detect while said array of one-dimensional detector units is kept still with respect to said object.

9. The scanning-based radiation detector apparatus of claim 1 wherein said short period of time, during which said array of one-dimensional detector units detects ionizing radiation before or during an initial part of the movement, is in the interval 100 ns–10 s.

10. The scanning-based radiation detector apparatus of claim 9, wherein the interval is 1 $\mu$s–100 ms.

11. The scanning-based radiation detector apparatus of claim 9, wherein the interval is 10 $\mu$s–10 ms.

12. The scanning-based radiation detector apparatus of claim 1 wherein said control device contains a look-up table of desired signal strengths for various object characteristics or an algorithm for determining desired signal strengths for various object characteristics, and is adapted to receive a characteristic of the object, of which a two-dimensional image is to be recorded; and to calculate the optimum exposure time for each one of the repeated detections by means of multiplying said short period of time with the ratio of the desired signal strength and a signal strength as obtained from said detection of ionizing radiation before or during an initial part of the movement.

13. The scanning-based radiation detector apparatus of claim 12 wherein said various object characteristics include object thicknesses.

14. The method of claim 13, wherein the object is a compressed breast and the thicknesses are defined as thicknesses at a particular compression force.

15. The scanning-based radiation detector apparatus of claim 12 wherein said various object characteristics include estimated densities.

16. The method of claim 15, wherein the object is a breast and the estimated densities are defined as fat content versus content of other tissue.

17. The scanning-based radiation detector apparatus of claim 12 wherein said object is a compressed breast and said various object characteristics include compressed breast thickness changes as caused by a change in compression force.

18. The scanning-based radiation detector apparatus of claim 12 wherein said object is a compressed breast and said various object characteristics include the change of absorption as caused by a change in compression force.

19. The scanning-based radiation detector apparatus of claim 1 comprising a collimator with a controllable variable aperture arranged in the path of said ionizing radiation upstream of said object, wherein said control device is adapted to deduce from said detection of ionizing radiation before or during an initial part of the movement an outer shape of said object; and to control the variable aperture of a shielding device to shield radiation not transmitted through or scattered off said object, and said shielding device is arranged to be fixed with respect to said array of one-dimensional detector units during movement of said array of one-dimensional detector units relative to said object.

20. The scanning-based radiation detector apparatus of claim 1 comprising a filter device with a controllable variable spectral transmission characteristics arranged in the path of said ionizing radiation upstream of said object, wherein said control device is adapted to deduce from said detection of ionizing radiation before or during an initial part of the movement a measure indicative of the contrast of the detection; and to control the variable spectral transmission characteristics of the filter device in response to said measure indicative of the contrast of the detection.

21. The scanning-based radiation detector apparatus of claim 1 comprising an X-ray tube for producing the ionizing radiation, said X-ray tube having a cathode which emits electrons and an anode on which said electrons impinge and which is a source of X-rays, said tube having an controllable variable operating voltage which is the voltage drop between said anode and said cathode, a tube current which is the current between said anode and said cathode, and a focal spot size which is the area of said anode on which said electrons impinge, wherein said control device is adapted to control the variable operating voltage of the X-ray tube in response to said detection of ionizing radiation before or during an initial part of the movement.

22. The scanning-based radiation detector apparatus of claim 1 comprising an X-ray tube for producing the ionizing radiation, said X-ray tube having a cathode which emits electrons and an anode on which said electrons impinge and which is a source of X-rays, said tube having an controllable variable operating voltage which is the voltage drop between said anode and said cathode, a controllable variable tube current which is the current between said anode and said cathode, and a focal spot size which is the area of said anode on which said electrons impinge, wherein said control device is adapted to control the variable tube current of the X-ray tube in response to said detection of ionizing radiation before or during an initial part of the movement.

23. The scanning-based radiation detector apparatus of claim 1 comprising an X-ray tube for producing the ionizing radiation, said X-ray tube having a cathode which emits electrons and an anode on which said electrons impinge and which is a source of X-rays, said tube having an controllable variable operating voltage which is the voltage drop between said anode and said cathode, a controllable variable tube current which is the current between said anode and said cathode, and a controllable variable focal spot size which is the area of said anode on which said electrons impinge, wherein said control device is adapted to control the variable focal spot size of the X-ray tube in response to said detection of ionizing radiation before or during an initial part of the movement.

24. The scanning-based radiation detector apparatus of claim 1 wherein said plurality of one-dimensional detector units is distributed in a two-dimensional pattern on a common support structure.

25. The scanning-based radiation detector apparatus of claim 1 wherein said plurality of one-dimensional detector units are sited in rows and stacks, the rows being parallel with the one-dimensional detector units and the stacks being essentially orthogonal thereto, where the one-dimensional detector units in each row are together capable of detecting completely the object in one dimension.

26. The apparatus of claim 25 wherein the one-dimensional detector units of each row are staggered with an overlap between adjacent one-dimensional detector units in the direction of the row.

27. The scanning-based radiation detector apparatus of claim 1 wherein said plurality of one-dimensional detector units are arranged in a circle, each oriented essentially radially with respect to said circle.

28. The scanning-based radiation detector apparatus of claim 1 wherein each of said plurality of one-dimensional detector units is a gaseous-based ionizing radiation detector, wherein electrons released by interactions between radiation photons and the gas can be extracted in a direction essentially perpendicular to the ionizing radiation entered into that one-dimensional detector unit.

29. The scanning-based radiation detector apparatus of claim 1 comprising a collimator of a radiation-absorbing material arranged in the path of said ionizing radiation upstream of said object, which collimator includes a plurality of radiation transparent slits, the number of the radiation transparent slits corresponding to the number of one-dimensional detector units, wherein the radiation transparent slits are aligned with the one-dimensional detector units, such that essentially planar ray bundles as transmitted through the radiation transparent slits of the collimator irradiate the respective one-dimensional detector units, and wherein said collimator is arranged to be fixed with respect to said array of one-dimensional detector units during movement of said array of one-dimensional detector units relative to said object.

30. The apparatus of claim 1, wherein said plurality of one-dimensional detector units are distributed in a dense array.

31. The apparatus of claim 1, wherein said apparatus, during said short period of time before or during an initial part of the movement, provides macroscopic structure information of the whole object area to be imaged.

32. The apparatus of claim 1, wherein said plurality of one-dimensional detector units comprises at least 10 one-dimensional detector units arranged, one after the other, in a direction of the movement by said device for moving.

33. The apparatus of claim 1, wherein said plurality of one-dimensional detector units comprises between 40 and 100 one-dimensional detector units arranged, one after the other, in a direction of the movement by said device for moving.

34. The apparatus of claim 1, wherein said plurality of one-dimensional detector units comprises between one-dimensional detector units arranged, one after the other, in a direction of the movement by said device for moving and with a separation distance of 5 mm.

35. The apparatus of claim 1 wherein said two-dimensional image of said object to be detected, and over a main part of which said one-dimensional images of ionizing radiation from said array of said plurality of one-dimensional detector units are distributed, measures between 20×20 and 50×50 $cm^2$.

36. A method for recording a two-dimensional image of an object comprising the steps of:
providing a scanning-based radiation detector apparatus comprising a plurality of one-dimensional detector units, each being arranged for one-dimensional imaging of the respective ionizing radiation, to which it is exposed, wherein the plurality of one-dimensional detector units are distributed in an array such that the one-dimensional images of the ionizing radiation from the plurality of one-dimensional detector units are distributed over a substantial portion of the two-dimensional image to be recorded;
detecting ionizing radiation, as transmitted through or scattered off said object, during a short period of time;
calculating an optimum exposure time for each one of repeated detections based on said detection of ionizing radiation during a short period of time; and
moving the array of the plurality of one-dimensional detector units relative to said object while exposing the plurality of one-dimensional detector units to ionizing radiation, as transmitted through or scattered off said object, and detecting repeatedly using said calculated optimum exposure time to thereby create a two-dimensional image of the object.

37. The method of claim 36 wherein said optimum exposure time is calculated based on a minimum or average signal value as obtained from said detection of ionizing radiation during a short period of time.

38. The method of claim 36 wherein said optimum exposure time is calculated based on a minimum or average signal value within a region of said array of one-dimensional detector units as obtained from said detection of ionizing radiation during a short period of time.

39. The method of claim 36 wherein said optimum exposure time is calculated based on an integrated signal value of one or some of the one-dimensional detector units of said array of one-dimensional detector units.

40. The method of claim 39, wherein said optimum exposure time is calculated based on the unit with lowest integrated signal value, as obtained from said detection of ionizing radiation during a short period of time.

41. The method of claim 36 wherein said array of one-dimensional detector units is moved relative to said object continuously, while detecting repeatedly to create the two-dimensional image of the object.

42. The method of claim 41 wherein said array of one-dimensional detector units is moved relative to said object at a speed, which is based on said calculated optimum exposure time.

43. The method of claim 36 wherein said array of one-dimensional detector units is moved stepwise relative said object, and said repeated detection using said calculated optimum exposure time is performed between each step of movement, while said array of one-dimensional detector units is kept still with respect to said object.

44. The method of claim 36 wherein said short period of time, during which said array of one-dimensional detector units detects ionizing radiation before or during an initial part of the movement, is in the interval 100 ns–10 s.

45. The method of claim 44, wherein the interval is 1 $\mu$s–100 ms.

46. The method of claim 44, wherein the interval is 10 $\mu$s–10 ms.

47. The method of claim 36 wherein;
a characteristic of the object, of which a two-dimensional image is to be recorded, is received;
a desired signal strength for the object, of which a two-dimensional image is to be recorded, is established by means of referring to a look-up table of desired signal strengths for various object characteristics or by means of an algorithm; and
said optimum exposure time for each one of the repeated detections is calculated by means of multiplying said short period of time with the ratio of the desired signal strength and a signal strength as obtained from said detection of ionizing radiation during a short period of time.

48. The method of claim 36 comprising the steps of:
arranging a shielding device with a variable aperture in the path of said ionizing radiation upstream of said object;

deducing an outer shape of said object from said detection of ionizing radiation during a short period of time; and adjusting the variable aperture of said shielding device to shield radiation not transmitted through or scattered off said object, wherein a collimator device is fixed with respect to said array of one-dimensional detector units during the step of moving said array of one-dimensional detector units relative said object.

49. The method of claim 36 comprising the steps of:

arranging a filter device with variable spectral transmission characteristics in the path of said ionizing radiation upstream of said object;

deducing from said detection of ionizing radiation before or during an initial part of the movement a measure indicative of the contrast of the detection; and adjusting the variable spectral transmission characteristics of said filter device in response to said measure indicative of the contrast of the detection.

50. The method of claim 36 comprising the steps of:

producing said ionizing radiation by means of an X-ray tube having a cathode which emits electrons and an anode on which said electrons impinge and which is a source of X-rays, said tube having an variable operating voltage which is the voltage drop between said anode and said cathode, a tube current which is the current between said anode and said cathode, and a focal spot size which is the area of said anode on which said electrons impinge; and adjusting the variable operating voltage of the X-ray tube in response to said detection of ionizing radiation during a short period of time.

51. The method of claim 36 comprising the steps of:

producing said ionizing radiation by means of an X-ray tube having a cathode which emits electrons and an anode on which said electrons impinge and which is a source of X-rays, said tube having an operating voltage which is the voltage drop between said anode and said cathode, a variable tube current which is the current between said anode and said cathode, and a focal spot size which is the area of said anode on which said electrons impinge; and adjusting the variable tube current of the X-ray tube in response to said detection of ionizing radiation during a short period of time.

52. The method of claim 36 comprising the steps of:

producing said ionizing radiation by means of an X-ray tube having a cathode which emits electrons and an anode on which said electrons impinge and which is a source of X-rays, said tube having an operating voltage which is the voltage drop between said anode and said cathode, a tube current which is the current between said anode and said cathode, and a variable focal spot size which is the area of said anode on which said electrons impinge; and adjusting the variable focal spot size of the X-ray tube in response to said detection of ionizing radiation during a short period of time.

53. The method of claim 36 wherein said plurality of one-dimensional detector units is provided in a two-dimensional pattern on a common support structure.

54. The method of claim 36 wherein said plurality of one-dimensional detector units are provided in rows and stacks, the rows being parallel with the one-dimensional detector units and the stacks being essentially orthogonal thereto, where the one-dimensional detector units in each row are together capable of detecting completely the object in one dimension.

55. The method of claim 54 wherein the one-dimensional detector units of each row are staggered with an overlap between adjacent one-dimensional detector units in the direction of the row.

56. The method of claim 36 wherein said plurality of one-dimensional detector units are arranged in a circle, each oriented essentially radially with respect to said circle.

57. The method of claim 36 wherein each of said plurality of one-dimensional detector units is a gaseous-based ionizing radiation detector, wherein electrons released by interactions between radiation photons and the gas is extracted in a direction essentially perpendicular to the ionizing radiation entered into that one-dimensional detector unit.

58. The method of claim 36 comprising the step of:

arranging a collimator of a radiation-absorbing material in the path of said ionizing radiation upstream of said object, which collimator includes a plurality of radiation transparent slits, the number of the radiation transparent slits corresponding to the number of one-dimensional detector units; and aligning the radiation transparent slits with the one-dimensional detector units, such that essentially planar ray bundles as transmitted through the radiation transparent slits of the collimator irradiate the respective one-dimensional detector units, wherein said collimator is fixed with respect to said array of one-dimensional detector units during the step of moving said array of one-dimensional detector units relative said object.

* * * * *